United States Patent [19]
Galy

[11] 4,453,926
[45] Jun. 12, 1984

[54] SCARIFIER

[75] Inventor: Michel G. H. Galy, St. Loup, France

[73] Assignee: Institut Merieux, Societe Anonyme, Lyons, France

[21] Appl. No.: 500,289

[22] Filed: Jun. 2, 1983

Related U.S. Application Data

[63] Continuation of Ser. No. 228,165, Jan. 26, 1981, abandoned.

[30] Foreign Application Priority Data

Jan. 31, 1980 [FR] France ............................... 80 02128

[51] Int. Cl.³ ........................................... A61B 17/20
[52] U.S. Cl. .................................... 604/47; 128/333; 206/367
[58] Field of Search .................. 128/329 R, 314, 315, 128/333, 743; 604/22, 46, 47, 263, 403; 206/570, 367, 438

[56] References Cited

U.S. PATENT DOCUMENTS

| | | | |
|---|---|---|---|
| 2,522,309 | 9/1950 | Simon | 128/253 X |
| 3,221,739 | 12/1965 | Rosenthal | 128/253 |
| 3,246,647 | 4/1966 | Taylor et al. | 128/253 |
| 3,291,129 | 12/1966 | Burelle et al. | 128/253 |
| 3,556,080 | 1/1971 | Hein | 128/743 |
| 3,596,660 | 8/1971 | Melone | 128/253 |
| 3,675,766 | 7/1972 | Rosenthal | 604/47 X |
| 4,109,655 | 8/1978 | Chacornac | 128/253 |

Primary Examiner—Michael H. Thaler
Attorney, Agent, or Firm—Norman Lettvin

[57] ABSTRACT

An improved packaging and assembly is provided for a multiple-point scarifying device for vaccinating or skin testing. In order to insure economic wage of immunological or allergenic liquid pre-assembled on the scarifying device, each cluster of multiple points is assembled with a removable surrounding envelope that achieves a hermetic seal with its mounting and which presents a transverse annual attachment wall to which an envelope-closing lid is hermetically secured after a limited quantity of liquid is deposited into the limited volume chamber surrounded by the envelope.

18 Claims, 7 Drawing Figures

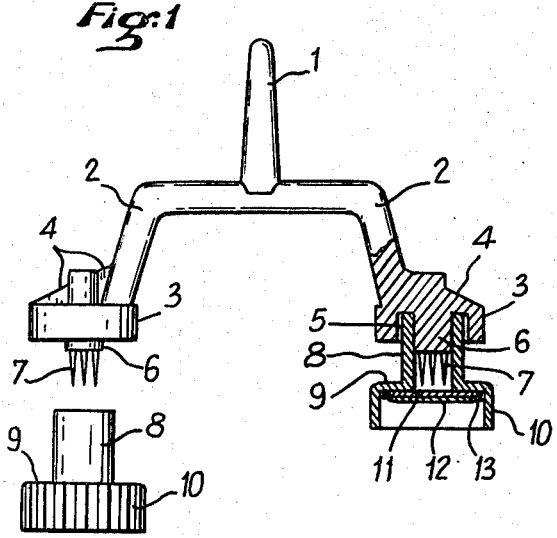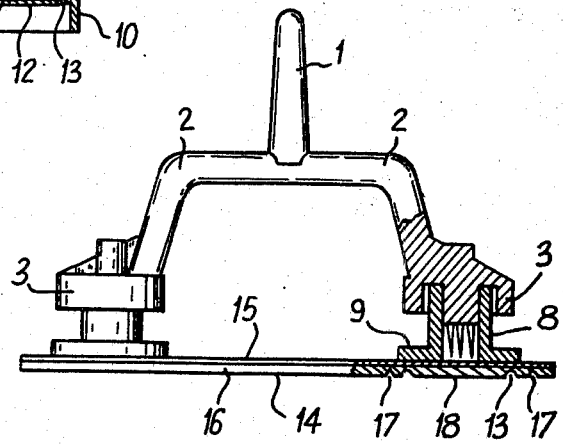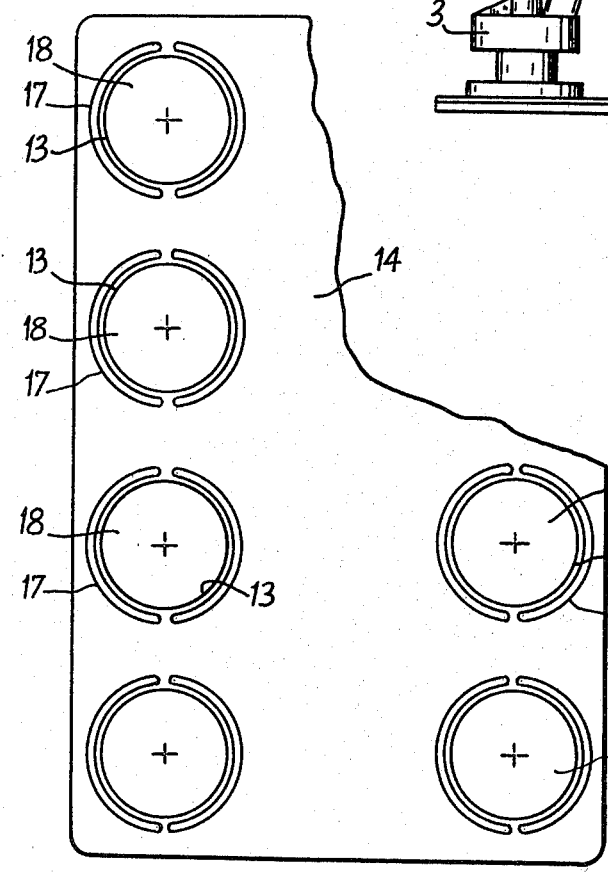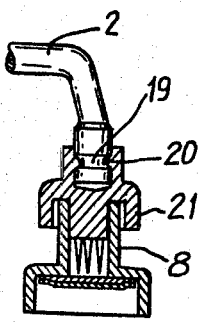

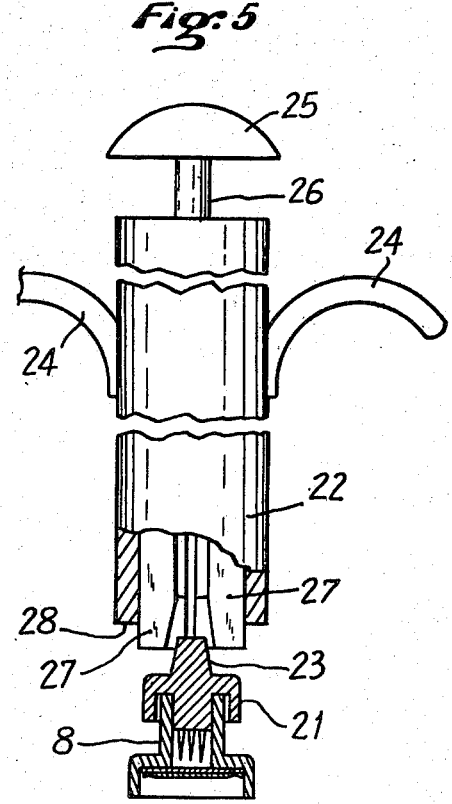
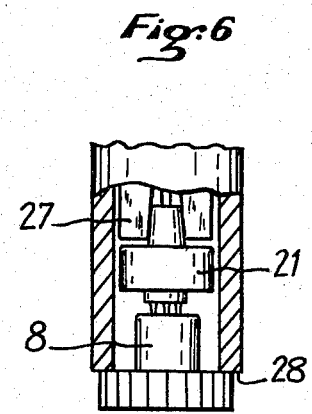
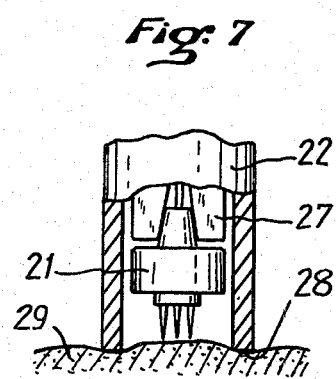

SCARIFIER

This application is a continuation of pending application, Ser. No. 228,165, filed Jan. 26, 1981 and now abandoned.

FIELD OF THE INVENTION

The present invention relates to a scarifying device of the type which has a plurality of points, meant for the scarifying of the skin, especially for vaccinations, cutireactions, immunological tests or allergy tests, and especially in one form for providing multiple units for executing multiple tests.

BACKGROUND OF THE INVENTION

There is known, from the prior art, scarifying devices to perform vaccinations or medical tests comprising, on a support suitable for prehension, or manual manipulation, by an operator, the provision of a cluster of scarifying points that are surrounded, or enclosed, with a removable tube which makes it possible to maintain inside the tube a substance that is to be held in contact with the points by capillarity. See. U.S. Pat. Nos. 3,136,314 and 3,291,129. The enclosing removable tube provides an aseptic and hermetically closed wrapping.

There is also known, from the prior art, scarifying devices meant for multiple tests, comprising a relatively rigid elongated handle from which there extend, arched or curved connecting rods in the manner of legs, each one of which terminates in a base from which extends a cluster of points. See U.S. Pat. No. 3,556,080.

As shown in FIG. 5 of U.S. Pat. No. 3,556,080 the points of the various clusters may be impregnated, or loaded, with the respective active substances through use of a separate base part which is shaped and formed to present a plurality of wells corresponding with the number of point clusters, and containing the respective substances, with each cluster of points being immersed into one of the wells in the base. The need for such a base may be eliminated by the modified construction that is shown in FIG. 6 of said patent, wherein the custer of points is surrounded by a removable deformable tube which contains the liquid substance which is maintained in contact with the cluster of points. In the latter construction the end of the tube that is distal from the point cluster has been pinched together and sealed, so as to form for the liquid substance an aseptic, tightly closed, and removable enclosure. Such an arrangement, however, presents a number of drawbacks. First, such a construction may result in excessive use, and wasteage, of expensive active substances such as antigens, allergens, medicines or test substances. In addition, the construction shown in the patent presents a substantial spatial bulk because the ends of the tubes, which are shown sealed, must be located far enough from the opposite tube ends which surround the points, in order to avoid tube deformation adjacent the tube ends adjacent the points. In addition, the prior art arrangement does not guarantee an absence of influence, of the operation of heat sealing the distal end of the tube, on the active substance, which by reason of an adjacent heat could be rendered either partially or entirely denatured.

The present invention has, therefore, as its purpose to avoid the said drawbacks of the prior act, and to supply a construction that makes it possible to appreciably decrease the waste of active test substances, to assure the presence of liquid where needed in a spatially tight closing and the integrity of same, while presenting a package of reduced spatial bulk.

The invention further has as its purpose to make it possible to perform, by automatic means, the assembly of the test device including setting into place and the protection of the active substances, and to improve the stability and the appearance of the assembled device.

SUMMARY OF THE INVENTION

According to one of the variations disclosed herein, the invention makes it possible for the scarifying device to be more flexibly used with selective subassemblies of active substances which are to be individually chosen or combined by a user.

The present invention has as an object the providing of a scarifying device comprising at least one group of elongated, closely spaced, or clustered, points which extend from a support that is connected to prehension means, said clustered group of points being surrounded by an envelope, preferably a cylindrical one, closed and attached in a hermetic, but removable manner to the point support, and characterized by the fact that said envelope presents a cylindrical wall which extends parallel to the points and which surrounds same, projecting from its first supported end toward its second end that is located in a plane located only slightly beyond the end of said points, and which turns and continues, at that point, to provide a central base surrounded by an annular shoulder which projects radially away from the points so as to form a surface adapted to receive there against a closure, or lid, both for obturating of said central chamber, or passage, and which also provides for a hermetical closure of said surface at a region radially spaced from said central chamber.

Thus the envelope advantageously presents a portion that is cylindrical in shape and meant to surround the cluster of points, with the free end of the cylinder capable of being fixed against the support for the points, for example by said free end penetrating by force fit into a circular groove provided in the support and which surrounds the base of the points, and with the other end of the cylindrical part shaped to extend radially in the form of a flat ring, leaving in its center a passage, or chamber, which gives access to the points, the closing lid being executed in the form of a flat disc made for securement to the ring-shaped envelope part adjacent the outer periphery of same. The volume, or space, surrounding the points is, by said construction, reduced to a strict minimum, and consequently, so is the quantity of active liquid substance in which the points are immersed.

Advantageously, the outer periphery of said ring-shaped part may be further extended axially to form a short cylindrical part with a greater outer diameter and forming, with the ring-shaped part, a kind of small annular cup against the bottom of which the closing lid is placed. Said cylindrical part with the greater outer diameter advantageously can present, on its exterior periphery gripping grooves or ribs which are meant to help in its manual handling.

Preferably, the said envelope is molded of a plastic material such as, for example, polyethylene, and the closing lid advantageously may comprise a layer of plastic material, in this instance polyethylene, preferably covered, on its external surface, with a protection material such as a metal film or a sheet of cardboard. The said closing lid preferably is affixed firmly to the corresponding annular surface, provided on the envelope, by means of heat sealing. Importantly, the circular line of heat securement of the closing lid to the envelope is spaced radially outwardly of the central portion of the closing lid which is in contact with the active substance, thereby eliminating increase in temperature at both said central part of the closing lid, and in the active substance, during the assembly operation of heat securing the closing lid in position.

It is possible, as a variation, to replace the heat welding or securement with other attachment means or processes, for example ultra-sonic welding, glueing, etc., but in all such operations the region of securement is located far enough from the active substance to prevent any changes in the nature of same.

In the cases where the envelope presents the shape of a small cup which receives and centers the closing lid in its bottom, the base of the small cup serves to protect the closing lid and its welding line from other mechanical contact, thus ensuring a protection of the closing lid and of the welding spots.

As already stated, a scarifying device that employs the present invention may include only a single cluster, or group, of points and consequently only a single envelope is required to surround the cluster. However, a scarifying device may also be executed in the form of a multiple scarifying device which makes it possible to perform, simultaneously, multiple reactions or vaccinations. Such device preferably comprises a relatively rigid, elongated, handle with transversely extending lateral supports located outwardly from the two longitudinal sides of the handle, with each support being connected to the handle by a connecting leg, preferably a curved or arched one, with each one of said supports carrying its own group, or cluster, of points. According to the invention herein, each group of points is surrounded with an envelope. Said envelope may present, at its base, a kind of small cup.

In a variation, the cup may provide an annular flange, which extends radially of the cylindrical wall of the envelope, and may have no cylindrical extension with a wider diameter than the envelope, and it may be executed in a perfectly plane manner with all of said annular flanges, the various envelopes of the device being arranged in the same plane. It is then possible to effect assembly of all closing lids simultaneously, that is to say the placing and the welding, or heat connecting, of the different closing lids, providing that all are executed from a single plate or sheet which is applied against the various bases, so as to cause the zones forming the closing lids, in the plate, to coincide with the corresponding bases. Preferably, the plate or sheet can remain whole, or as a unitary part, after the setting into place of the closing lids, to form a surface capable of carrying inscriptions. The closing lids, however, may be individualized in the plate, not only by means of their circular welding line, but also by pre-cuts or weakened zones surrounding that line. Advantageously, the base may be executed in the form of a film of plastic material, especially polyethylene, covered with a relatively stiff cardboard with, possibly, the inserting of a metallic sheet between the film and cardboard.

In another improved form of execution of the invention, the prehension means, for example the handle with its various tabs, or legs, each may carry an individual removable support, and each such support may carry its own envelope. In this way, during assembly one can set onto a plate, for connection onto the ends of the various tabs or legs, separate combination support-envelope units that each contain therein a substance of choice, and with the units assembled according to any arbitrary arrangement. Preferably, the point-carrying supports then have at their ends, for connection to a leg or tab, a rapid fixation or snap connection, for example by a force fit, for cooperation with the end of a tab shaped in a corresponding manner to effect the connection. The resistance to separation between a support and the end of its corresponding leg or tab will be made greater than the resistance to separation between the support and its corresponding envelope.

In another variant construction, a gripping means can advantageously be provided so as to cooperate with a single support that is provided with its own envelope, and such gripping means provides for rapid use and manipulation of said support and envelope. The said gripping means can advantageously be of the type having jaws able to fasten onto a portion of the support opposite to the end carrying the points. These jaws can, for example, advantageously be caused to tighten around said portion by their sliding in a tubular member to bring about the fastening of the jaws by a ramp effect.

In a particularly advantageous manner, said gripping means can incorporate means making it possible, during operation, to separate the envelope from the support in order to expose the points and to also enable the operator holding the gripping means to thereafter carry out the scarification operation.

Other advantages and characteristics of the invention will become apparent from the following description, given only as an example which is not intended to be limitative, and with reference to the attached drawing.

BRIEF DESCRIPTION OF THE DRAWINGS

FIG. 1 is an end elevational, or profile, view of a scarifying device that is provided with a plurality of supports for clustered points according to the invention, and showing the envelope removed from the left hand support to expose the clustered points.

FIG. 2 is a view similar to FIG. 1, but showing a modified form of assemblage of the envelopes for cooperation with the plurality of supports for the clustered points, and utilizing a unitary sheet, or plate to which the plurality of envelopes attach.

FIG. 3 is a fragmentary bottom plan view of the plate, or sheet, of closing lids for the form of device shown in FIG. 2. FIG. 4 is a fragmentary cross-sectional view of a further modification of FIG. 1, showing both a removable support for clustered points and a removable envelope, as in FIG. 1, for use with said removable support.

FIG. 5 is a fragmentary elevantional and cross-sectional view showing a variant gripping construction for handling and manipulating a single scarifying device that is packaged with a removable envelope.

FIG. 6 is a fragmentary view, illustrating portions of the combination shown in FIG. 5 at a point in time when the scarifying device is held by the gripping construction while the envelope is being removed from the support.

FIG. 7 a view similar to that of FIG. 6 showing the scarifier positioned just prior to scarification.

DESCRIPTION OF THE PREFERRED EMBODIMENTS OF THE INVENTION

With reference first to FIG. 1, the device there represented, meant particularly to make it possible to execute a plurality of immunization tests or of allergy tests, is molded of a plastic, such as polymethacrylate of methyl. It provides a handle 1 which is seen in edgewise profile in FIG. 1 and normally extends longitudinally in a direction perpendicular to the view shown. Said handle presents, on each side of its median plane, a plurality of legs, or tabs, 2 comprising a first horizontal section which extends perpendicular to handle 1, and a second oblique section extending downwardly. At the lower and extended end of each one of the oblique sections of tabs 2, there is located a support 3, generally circular in shape. What has been described is integrally molded as a body, providing the whole of the unit, and presenting, in addition, a stiffening rib 4 located in the plane of each tab 2. The lower tab portion of the circular support 3 is shaped to provide therein a circular groove 5 which surrounds a molded central base 6, that is shaped and arranged to provide, integrally thereon, a group, or cluster, of points 7, which are shown pointing downwardly.

The envelope which surround each group of points 7 includes a cylindrical first part 8, the internal diameter of which corresponds to the external diameter of the base 6, so as to permit the envelope to be pressed into place by a press, or slight force, fit of said cylindrical part 8 onto the base 6 and around points 7, and this fit extends over axial distance that is sufficient, because of the axial depth of groove 5, to ensure a hermetic juncture between the inner surface of cylindrical part 8 and the radially inner wall of groove 5 that is part of base 6. As best seen in FIGS. 1, 2 and 4, the radial width of groove 5 is substantially greater than the radial thickness of the wall of the cylindrical part. At the end of the envelope remote from support 3, the cylindrical part 8 of polyethylene is shaped to provide a flat ring-shaped, or annular, shoulder 9 which lies in a plane transverse to cylindrical part 8 and which continues and projects, in the downward direction, to provide a second cylindrical part 10, the diameter of which is greater than the diameter of part 8, but the axial length of which is less then the axial length of part 8. As seen on the envelope that has been separated from its support, which appears to the left of FIG. 1, said second cylindrical portion 10 is provided on its exterior with alternating grooves and ribs to increase its prehension, or manual gripping.

As seen in the cross-section on the right of FIG. 1, the length of the internal opening, or central chamber, of first part 8 is constructed so that, when the upper edge of first part 8 abuts the bottom of groove 5, the plane of the extended, or lower edge of cylindrical part 8 is located spaced slighty from the terminal ends of points 7. When the envelope has thus been mounted over the base 6, it is thus possible to place in the bottom of the small cup, formed by the flat ring-shaped, or annular, bottom part 9 surrounded by the peripheral edge 10, a circular disc-shaped closing lid comprising a polyethylene sheet 11 externally covered with an aluminum sheet 12. Said closing lid is heat welded, or otherwise adhered, at its outer periphery, along a circular trace at 13, against the bottom wall of the small cup, close to the cylindical portion 10.

The filling of each chamber surrounded by cylindrical first part 8 is executed in the following manner. There is set into place on each support 6, that is to say around each group of points 7, an envelope without its closing lid. The whole assemblage is then sterilized, such as by gas sterilization, and it is turned over, or invested, so that the handle is oriented downward, and the points are oriented upwardly. The spaces, or volumes, adjacent to the points inside each part 8, are filled with the various active liquid substances, referred to as biologic substances, that is to say one substance per group of points. The filling is such that the points are then immersed in the biologic substance. There are then set into place, in the small cups, the various closing lids 11-12, and same are secured in position by welding or heat sealing, or by other means. It can be understood that, by reason of the foregoing operations there has been set into place in each chamber only a limited quantity of active substance the volume of which is limited between the base 6, the wall 8 and the closing lid. In addition, welding is performed on the circular line, 13, radially removed from the internal volume containing the substance, so that substantially no heat transmission occurs toward said substance.

The device thus executed can then be conditioned in simple wrappings or packaging. Also, it can be arranged that the bases of the envelopes, formed by the lower edge of cylindrical parts 10, extend into, and lie in, the same plane and form, for the whole device, a stable base.

When an operator wishes to use the device, possibly after having removed it from its wrapping, he seizes it by handle 1, with one hand, and with the other hand he removes in succession each of the various envelopes, so as to expose the totality of the groups of points such as 7. The device is then ready for the scarifying operation.

In order to provide an alternative means for the individual removal of envelopes, there may be provided a continuous plate of cardboard or of plastic material (not shown), in which there are, at the level of the cylindrical parts 8, a number of perforations, or openings, the diameter of which is only slightly greater than the external diameter of the cylindrical parts 8, said part then being moved so as to captured between the opposing surfaces 9 and the lower terminal edges of supports 3, so that by pulling that single part downwardly, away from handle 1, the various envelopes will all be simultaneously removed.

With reference to FIGS. 2 and 3, in that modified form of modified device, the envelopes still comprise a cylindrical body 8 and a ring-shaped part 9, but they do not have the widened cylindrical part 10. The inferior, or distal, faces of the ring-shaped parts 9 then lie substantially in one plane. The closing of all the various envelopes of the device is obtained by means of a single closure plate 14 formed of a polyethylene sheet 15 backed by a relatively stiff cardboard cover 16. Arcuate partial cut-outs 17, suitably placed to be located opposite supports 3, aid in surrounding sections designated as closing lids 18, which are adapated to be simultaneously welded, or heat sealed, against the lower faces of the various parts 9, along weld lines 13, after the device has received the various desired quantities of the different substances placed into the corresponding chambers, or envelopes, provided around each group of points. By this construction, removal of the single plate 14, when the device of FIG. 2 is inverted, operates to expose each cluster of points 7 simultaneously for use.

The partial cut-outs 17 are conceived and are to be provided so as to make possible, after welding connection, the separation of the remainder of plate 14, and to let subsist only the welded closing lids, against the envelopes. However, as a further variation, the plate 14 may be designed in such a way that it can stay permanently and make it possible to separate only certain envelopes from the supports 6, two by two for example, when the resistance of the welding is greater that the resistance of the fixation of the envelope 8 in groove 5.

With reference to FIG. 4, in this form of the construction there is shown a tab 2 which presents at its free terminus a section provided with a transverse annular depression or groove 19. Said groove 19 is meant to cooperate by a press-fit type, or snap, connection with an internal bead, or swelling 20 corresponding in size and shape with groove 19 and provided on molded support 21 which presents, for the rest of the part, the same shape as support 3. Said support 21 connects to an envelope having a cylindrical part 8 fitted with a closing lid as shown in FIG. 1. The resistance to axial separation between the tab, or leg, 2 and support 21 is designed to be greater than the resistance to axial separation between the support 21 and the envelope which surrounds the points.

Thus, it is possible to deliver to the user devices for scarifying which present a handle similar to handle 1, and a plurality of tabs 2 free from supports at their ends, as well as individual units constituted, each one of them, by a support 21 covered with its envelope and containing therein a specific substance. The user can then set, at the desired locations on the handle-tab device, the support envelope units which contain the required substances. Then, after separation of the envelopes, while the supports remain fixed to the tabs, the scarifying device is ready to be used. After use, supports 21 are separated from the device itself which can then be used again after new units have been set into place.

In the embodiment or combination of FIGS. 5, 6 and 7, and in the use of a scarifier having a single group of points, there is shown a support 21 that is constructed to be able to cooperate with an instrument that is adapted to receive and support, in a rapid and detachable manner, a scarifier support with its group of points. The scarifier support 21 is similar to the support shown in FIG. 4, and the group of points is protected by removable envelope 8. Unlike the specific support 21 of FIG. 4, the support of FIG. 5 has, at its end opposite to the groups of points, a frustro conical extension 23 with a limited slope.

The gripping instrument means 22 is in the form of an elongated body, provided with two opposite finger support clips 24 and an upper control button 25 that connects to a slide rod 26. The movement of rod 26 makes it possible to axially drive, or move, a group of jaws 27, for example four jaws which, in the manner well known in the propelling pencil field, tend to move radially away from one another when rod 26 is forced downward by button 25, whereas the jaws 27 tend to close when rod 26 is again driven axially upwards under the action of a conventional opposing spring.

Thus, operation is as follows. The operator engages the gripping instrument means 22 with two fingers that engage clips 24. He then presses button 25 axially downwardly with the thumb and, counter to the action of the opposing spring, slides jaws 27 downwards, which also causes said jaws to move apart to the extreme position shown in FIG. 5 in which the ends of jaws 27 emerge or project from body 22 beyond its extreme edge 28. As shown in FIG. 5, the operator then moves instrument 22 to a position where jaws 27 surround extension 23 of the support 21. The operator then relaxes the pressure on button 25 which causes both an upward and inward movement of the jaws 27 to a position gripping extension 23. At the same time the assembly consisting of support 21 and envelope 8 is displaced upward and inward of the body of gripping instrument means 22. FIG. 6 shows the extreme upper position of jaws 27. It can be seen that the diameter of the internal space in which jaws 27 slide is selected to be smaller than the widest diameter portion of envelope 8, causing envelope 8 to abut against rim 28. As a result of the upward movement of the jaws 27 and the support 21 to the position seen in FIG. 6, the envelope 8 is automatically separated from support 21 in such a way that envelope 8 drops, under force of gravity, and the points of the scarifier are then exposed.

The operator may then apply end 28 against the epidermis 29 of the patient, as seen in FIG. 7, and then operates button 25 bringing about a downward movement of jaws 27 and the support 21. As a result, the exposed points penetrate the epidermis, and scarification takes place. Following scarification, the operator removes the gripping means 22 from the epidermis and, whilst continuing to press button 25 downwards, moves the jaws 27 apart and drops support 21. The operator is then able to take another support 21 provided with its envelope 8. The supports 21 can advantageously be arranged successively on a belt, carton or any other member in an unchanging order, corresponding to the different substances to be used.

Although the present invention has been described for limited particular forms or designs as shown and described, it is well understood that the invention claimed herein is not to be limited solely to said forms, and that the inventions may be subject to various modifications in form, shape, or material without falling outside the invention's scope or spirit.

I claim:

1. In a scarifying device that includes at least one imperforate support having a plurality of parallel points projecting therefrom, and an elongated cylindrical sleeve removably mounted on said support for surrounding the points and adapted for hermetically holding a supply of active substance only between said support and sleeve; the improvement comprising, in combination:

envelope means including said elongated sleeve being initially open at both ends thereof, one open end of which is assembled onto, and constructed to cooperate with, said support, to provide a substantially hermetic seal with the portion of the support from whence the points project, while said other open end of said envelope means remains open to permit subsequent introduction thereinto of a supply of an active substance;

said elongated, open ended, sleeve projecting from its said end that is assembled onto the support in a direction and manner to surround the points and to provide that the other open end of said sleeve is located spaced beyond the tips of the points that project from the support;

a transverse annular wall provided at said other end of said cylindrical sleeve and extending radially outwardly of the sleeve, said annular wall providing a planar attachment surface thereon;

the length of said cylindrical sleeve being such that said planar attachment surface of the annular wall is located in a plane spaced distally from said support, and closely to but beyond a plane through the terminii of the points, whereby the cylindrical sleeve together with the support for the points cooperate to define a cup-shaped, open-ended, limited volume chamber into which an active substance may be introduced;

a selected amount of an active substance deposited into said elongated sleeve of the envelope means that is assembled onto the support, to immerse said points in said active substance;

and closure cap means, separate from the cylindrical sleeve, being secured to said planar attachment surface of the annular wall to overlie the central open space of the other end of said cylindrical sleeve to maintain the active substance in position during storage and prior to usage.

2. A construction in claim 1 wherein the closure cap is heat sealed to the annular wall along a peripheral line that surrounds and is spaced radially outwardly of the periphery of the bore through the cylindrical sleeve.

3. A construction as in claim 2 wherein the outer periphery of the annular wall of the envelope means has a sleeve extending axially therefrom to provide a grip means for selectively manually removing the cylindrical sleeve from the support when it is desired to expose the cluster of points with active substance carried thereon.

4. A construction as in claim 3 wherein the outer surface of the sleeve is provided with means to enhance manual gripping of the sleeve.

5. A construction as in claim 1 wherein the scarifying device includes a handled apparatus operatively associated with a plurality of spaced supports of the type defined, each support having closely spaced parallel points projecting therefrom; and said closure cap means comprising a single sheet means, of a dimensional size to overlay each of the attachment surfaces of each of the cylindrical sleeves for said plurality of supports, and said sheet means being secured to each of said attachment surfaces to provide closure cap means for each of said cylindrical sleeves.

6. A construction as in claim 5 wherein the closure cap portions of the sheet means are individualized by lines defined in the sheet means.

7. A construction as in claim 1 wherein the scarifying device is molded of polymethyl methacrylate and the envelope is formed from polyethylene.

8. A construction as in claim 1 wherein the closure cap means includes a polethylene layer that engages the envelope means and is heat sealed thereto, and a stiffening layer selected from cardboard or metal.

9. A construction as in claim 1 wherein the portion of the support opposite the spaced points thereon is provided with a shape that permits of selective detachable securement of the support to a mounting means therefor, and wherein the separation resistance at the point of detachable securement of the support to a mounting means is designed to be greater than the separation resistance between the envelope and the support.

10. A construction as in claim 9 wherein the shape that permits of selective detachable securement includes a ribbed recess in the support adapted for snap connection to a grooved member that is adapted to enter said recess.

11. A construction as in claim 9 wherein the shape that permits of selective detachable securement includes a frustro conical extension on the support adapted to be gripped by a plurality of separable jaws.

12. A construction as in claim 9 in combination with an instrument that provides an elongated body with a control button extending from one end and a recess at the other end for receiving thereinto the frusto conical extension of the support of the scarifier; a plurality of radially and axially movable jaws in said elongated body arranged for movement by the control button for gripping a scarifier support by its frusto conical extension, for stripping the envelope from the support to expose the scarifying points, providing means for effecting scarification with the exposed points, and for then discarding the used scarifier.

13. A device as set forth in claim 1 wherein the active substance is a liquid that provides a limited volume pool into which the points are immersed.

14. In a pre-packaged skin scarifying and biologic administering device that includes a support having a plurality of scarifying points projecting therefrom and an elongated closure member that is removably mounted on said support, in such a manner that upon separation of the closure member from the support, the scarifying points will retain thereon an amount of an active substance, to be administered by the device simultaneously with selective skin scarification by the points; the improvement comprising, in combination;

said closure member being in the form of an elongated tube initially open at both ends, with the tube opening at a first end of the tube being of a size to be press fit onto and to surround, in a fluid tight joint, the portion of said support from which the scarifying points project, and with said points projecting through said first end of the tube into the interior of said tube;

the other end of said tube being initially open and having an annular transverse wall thereat, formed integrally with said tube and extending radially outwardly of the tube's axial opening to provide a transverse mounting surface at the other end of said tube;

the length of said tube being limited to the extent that after said first end has been press fit onto the support for the scarifying points, said other end of the tube then extends only slightly past the terminal ends of the scarifying points, so that the tube and support together cooperate to define a cup-shaped, open-ended recess, into which the points project and so as to be adapted to be immersed into an active liquid substance that is entered into the tube through its said open other end;

a selected quantity of active substance entered into said tubular closure member only through said open other end of the tube after the tube is assembled on said support, so as to provide for the active substance to engage and be retained on the points and to have said points totally immersed in said active substance; and a planar closure member in the form of a disc that is initially separate from the elongated tube and is of an area dimension greater than the open other end of the tube, so as to overlie and close said opening at said other end of the tube, and which is secured onto the said annular transverse mounting surface after said selected quantity of active substance has been introduced into said tube.

15. A device as set forth in claim 14, wherein said annular transverse wall has a grip wall portion extending therefrom to serve as means for selectively removing the closure from the support.

16. A device as set forth in claim 15, wherein the grip wall portion is cylindrical and has an inner peripheral dimension that is greater than the peripheral edge dimension of the closure disc.

17. A device as set forth in claim 14, wherein the closure disc is secured to the annular transverse wall along a peripheral line of connection that surrounds and is spaced radially outwardly from, the inner periphery of the bore which confines the active substance therein.

18. A devices as set forth in claim 14 wherein the active substance is a liquid that provides a limited volume pool into which the points are immersed.

* * * * *